US00PP17416P2

(12) United States Plant Patent
Pinel

(10) Patent No.: US PP17,416 P2
(45) Date of Patent: Feb. 13, 2007

(54) ***HIBISCUS* PLANT NAMED 'BRICUTTS'**

(50) Latin Name: *Hibiscus syriacus*
Varietal Denomination: Bricutts

(75) Inventor: Pascal Pinel, D'Anjou (FR)

(73) Assignee: Spring Meadow Nursery Inc., Grand Haven, MI (US)

( * ) Notice: Subject to any disclaimer, the term of this patent is extended or adjusted under 35 U.S.C. 154(b) by 20 days.

(21) Appl. No.: 11/151,885

(22) Filed: Jun. 14, 2005

(51) Int. Cl.
*A01H 5/00* (2006.01)

(52) U.S. Cl. ..... Plt./257
(58) Field of Classification Search ..... Plt./257
See application file for complete search history.

(56) References Cited

PUBLICATIONS

UPOVROM Plant Variety Database 2006/01. Search for cultivar BRICUTTS.*

* cited by examiner

*Primary Examiner*—Anne Marie Grunberg
*Assistant Examiner*—Annette H Para
(74) *Attorney, Agent, or Firm*—C. A. Whealy

(57) ABSTRACT

A new and distinct cultivar of *Hibiscus* plant named 'Bricutts', characterized by its upright plant habit; freely branching habit; dense and bushy growth habit; and numerous, large, semi-double and white-colored flowers with red purple-colored centers and basal venation and numerous stamenoid petaloids.

1 Drawing Sheet

Botanical designation: *Hibiscus syriacus.*
Cultivar denomination: 'Bricutts'.

BACKGROUND OF THE INVENTION

The present Invention relates to a new and distinct cultivar of *Hibiscus* plant, botanically known as *Hibiscus syriacus,* and hereinafter referred to by the cultivar name Bricutts.

The new *Hibiscus* is a naturally-occurring branch mutation of the *Hibiscus syriacus* cultivar Notwoodone, disclosed in U.S. Plant Pat. No. 12,619. The new *Hibiscus* was discovered and selected by the Inventor in a controlled environment in St. Barthelemy D'Anjou, France in July, 2001. The new *Hibiscus* was selected on the basis of its flower coloration.

Asexual reproduction of the new *Hibiscus* by cuttings at St. Barthelemy D'Anjou, France, since July, 2001 has shown that the unique features of this new *Hibiscus* are stable and reproduced true to type in successive generations.

SUMMARY OF THE INVENTION

Plants of the cultivar Bricutts have not been observed under all possible environmental conditions. The phenotype may vary somewhat with variations in environment such as temperature, light intensity, daylength, and fertility level without, however, any variance in genotype.

The following traits have been repeatedly observed and are determined to be the unique characteristics of 'Bricutts'. These characteristics in combination distinguish 'Bricutts' as a new and distinct *Hibiscus* cultivar:

1. Upright plant habit.
2. When pinched, very freely branching habit; dense and bushy appearance.

3. Numerous, large, semi-double and white-colored flowers with red purple-colored centers and basal venation and numerous stamenoid petaloids.

Plants of the new *Hibiscus* differ primarily from plants of the parent, the cultivar Notwoodone, in flower color as plants of the cultivar Notwoodone have lavender-colored flowers.

Plants of the new *Hibiscus* can be compared to plants of the *Hibiscus* cultivar Notwoodtwo, disclosed in U.S. Plant Pat. No. 12,612. In side-by-side comparisons conducted in Grand Haven, Mich., plants of the new *Hibiscus* differed from plants of the cultivar Notwoodtwo in the following characteristics:

1. Plants of the new *Hibiscus* were smaller than plants of the cultivar Notwoodtwo.
2. Plants of the new *Hibiscus* and the cultivar Notwoodtwo differed in flower color as plants of the cultivar Notwoodtwo had pure white-colored flowers.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ from the color values cited in the detailed botanical description which more accurately describe the actual colors of the new *Hibiscus.*

The photograph at the bottom of the sheet comprises a side perspective view of a typical flowering plant of 'Bricutts' grown in a outdoor nursery.

The photograph at the top of the sheet comprises a close-up view of a typical flower of 'Bricutts'.

DETAILED BOTANICAL DESCRIPTION

In the following description, color references are made to The Royal Horticultural Society Colour Chart, 1995 Edition, except where general terms of ordinary dictionary significance are used. Plants used for the photographs and description were grown in Grand Haven, Mich. during the late summer and under full sun field conditions which closely approximate commercial production conditions. During the production of the plants, day temperatures ranged from 10 to 32° C. and night temperatures ranged from 4 to 24° C. Plants used for the description and photographs were about 2.5 years old.

Botanical classification: *Hibiscus syriacus* cultivar Bricutts.

Parentage: Naturally-occurring branch mutation of the *Hibiscus syriacus* cultivar Notwoodone, disclosed in U.S. Plant Pat. No. 12,619.

Propagation:

*Type cutting.*—By cuttings.

*Time to initiate roots.*—About three weeks at 32° C.

*Time to produce a rooted young plant.*—About eight weeks at 32° C.

*Root description.*—Thick and fleshy; 155A in color.

*Rooting habit.*—Freely branching.

Plant description:

*Form.*—Mostly upright; inverted triangle; dense and bushy perennial shrub.

*Plant height, soil level to top of plant plane.*—About 1 m.

*Plant width.*—About 65 cm.

*Vigor.*—Moderate to rapid growth rate; vigorous.

*Branching habit.*—When pinched, very freely branching with about 38 lateral branches per plant.

*Lateral branches.*—Length: About 55 cm. Diameter: About 4.5 mm. Internode length: About 6.3 cm. Texture: Smooth; slightly pubescent. Color: 137A.

*Foliage description.*—Arrangement: Alternate; simple. Quantity per lateral branch: Typically about 18. Length: About 6.2 cm. Width: About 3.5 cm. Shape: Rhomboid to ovate, three-lobed. Apex: Acute. Base: Broadly cordate to rounded. Margin: Coarsely dentate. Texture, upper and lower surfaces: Glabrous; smooth. Venation pattern: Palmate. Color: Developing foliage, upper surface: 144A. Developing foliage, lower surface: 144B. Fully expanded foliage, upper surface: 146A; venation, 146A. Fully expanded foliage, lower surface: 146B; venation, 146B. Petiole: Length: About 1 cm. Diameter: About 1.5 mm. Color: 146B.

Flower description:

*Flower type and habit.*—Semi-double rounded flowers arising from leaf axils. Freely flowering. Flowers last about one day on the plant. Not persistent. Not fragrant.

*Natural flowering season.*—Continuously flowering from mid-August through October in Grand Haven, Mich.

*Quantity of flowers/flower buds.*—About twelve per lateral branch; about 224 per plant.

*Flower diameter.*—About 10 cm.

*Flower depth (height).*—About 4.5 cm.

*Flower buds.*—Length: About 2.2 cm. Diameter: About 1.8 cm. Shape: Ovate. Rate of opening: About one day. Color: 146C.

*Petals.*—Arrangement/appearance: Single whorl of five petals; imbricate. Length: About 4.5 cm. Width: About 4.5 cm. Shape: Obovate. Apex: Obtuse to rounded. Margin: Entire; undulate. Texture, upper and lower surfaces: Smooth, glabrous. Color: When opening and fully opened flower, upper surface: 155D occasionally tinted with 59A; towards the base and basal venation, 59A. When opening and fully opened flower, lower surface: 155D. Petaloids: Variable shape and size. Quantity: About 15 to 35. Arrangement: Whorled. Length: About 2 cm. Width: About 8 mm. Shape: Mostly spatulate; margin, entire and undulate. Color: When opening and fully opened, upper surface: 155D occasionally tinted with 59A. When opening and fully opened, lower surface: 155D.

*Sepals.*—Arrangement: Five in a single whorl, fused; calyx, star-shaped. Length: About 1.7 cm. Width: About 6 mm. Apex: Acute. Margin: Entire. Color, upper and lower surfaces: 146B.

*Peduncle.*—Strength: Moderately strong. Angle: About 30° to the stem. Length: About 3 cm. Diameter: About 1.5 cm. Color: 138A.

*Reproductive organs.*—Stamens: Anther length: About 1 mm. Anther shape: Globular. Anther color: 155B. Pollen amount: Abundant. Pollen color: Close to 162A. Pistils: Pistil quantity per flower: One. Pistil length: About 3 cm. Stigma shape: Five-parted; rounded. Stigma color: 155D. Style length: About 3 cm. Style color: 155D. Ovary color: 155B.

*Seed.*—Seed development has been observed.

Disease/pest resistance: Under commercial production conditions, plants of the new *Hibiscus* have not been noted to be resistant to pathogens and pests common to *Hibiscus*.

Temperature tolerance: Plants of the new *Hibiscus* have been observed to tolerate temperatures from −25 to 38° C.

It is claimed:

1. A new and distinct cultivar of *Hibiscus* plant named 'Bricutts', as illustrated and described.

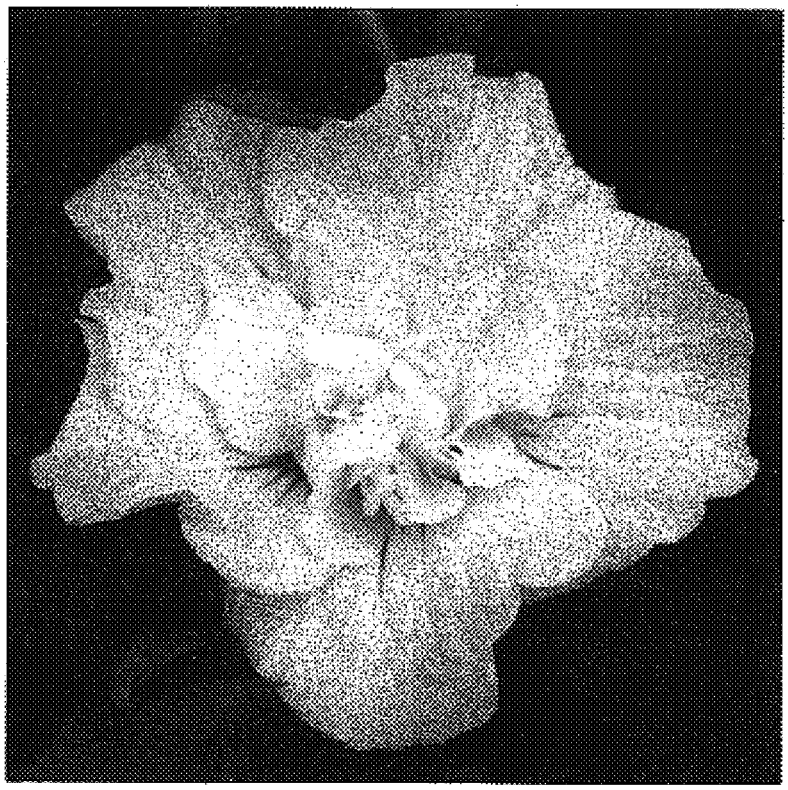
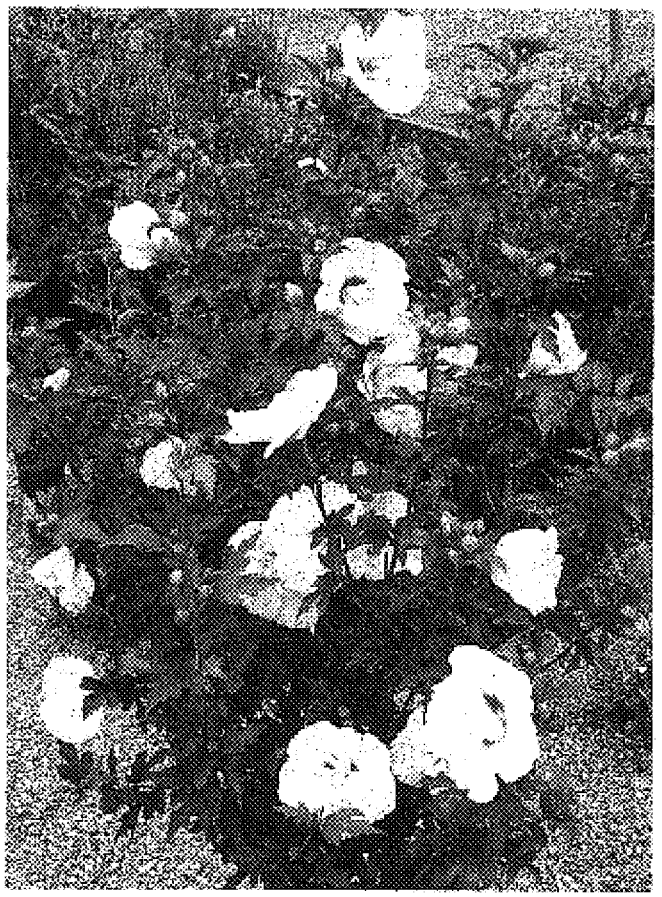

* * * * *